United States Patent
Overkleeft et al.

(10) Patent No.: US 6,376,468 B1
(45) Date of Patent: Apr. 23, 2002

(54) PROTEIN:PRENYL TRANSFERASE INHIBITORS

(75) Inventors: Herman Steven Overkleeft, Cambridge, MA (US); Steven Hendrik Leonard Verhelst, Vlaardingen (NL); Nicolaas Johannes Meeuwenoord, Voorschoten (NL); Elsbet Jantine Pieterman, Leiden (NL); Louis Hartog Cohen, Breukelen (NL); Mark Overhand; Gijsbert Arie Van der Marel, both of Leiden (NL); Jacobus Hubertus Van Boom, Oegstgeest (NL)

(73) Assignees: Nederlandse Organisatie Voor Toegepast-Natuurwetenschappelijk Onderzoek TNO, Delft (NL); Rijksuniversiteit Leiden, Leiden (NL)

( * ) Notice: Subject to any disclaimer, the term of this patent is extended or adjusted under 35 U.S.C. 154(b) by 0 days.

(21) Appl. No.: 09/497,402

(22) Filed: Feb. 3, 2000

(30) Foreign Application Priority Data

Feb. 3, 1999 (EP) .............................................. 99200316

(51) Int. Cl.$^7$ ...................... A61K 31/351; A61K 38/02; C07D 315/00; C07K 2/00; C12Q 1/48

(52) U.S. Cl. ............................. 514/18; 435/15; 514/19; 514/217.11; 514/217.12; 514/218; 514/237.5; 514/237.8; 514/315; 514/365; 514/374; 514/428; 514/432; 514/438; 514/452; 514/459; 514/475; 530/323; 530/331; 540/553; 540/610; 544/159; 546/246; 548/146; 548/215; 548/537; 548/558; 548/566; 548/567; 549/13; 549/76; 549/378; 549/424; 549/425; 549/427; 549/551; 549/553

(58) Field of Search ............................... 435/15; 514/18, 514/19, 212, 218, 237.5, 237.8, 315, 352, 354, 357, 365, 370, 371, 374, 377, 403, 423, 426, 432, 438, 447, 448, 452, 459, 471, 472, 475, 428, 217.11, 217.12; 530/323, 330, 331; 540/553, 575, 605, 606, 607, 610; 546/244, 245, 246, 247, 304, 309, 310, 312, 323, 335; 548/146, 194, 200, 215, 233, 371.7, 379.4, 537, 558, 566, 567; 549/13, 28, 68, 69, 72, 76, 378, 424, 425, 427, 480, 487, 493, 494, 548, 551, 553; 544/159

(56) References Cited

FOREIGN PATENT DOCUMENTS

WO 97/30053 * 8/1997

OTHER PUBLICATIONS

Herman S. Overkleeft et al., "Design and Synthesis of a Protein: Farnesyltransferase Inhibitor based on Sugar Amino Acids," Tetrahedron Letters 40 (1999), pp. 4103–4106.

Yimin Qian et al., "Design and Structural Requirements of Potent Peptidomimetic Inhibitors of p21$^{ras}$ Farnesyltransferase," The Journal of Biological Chemistry, vol. 269, No. 17, Apr. 29, 1994, pp. 12410–12413.

* cited by examiner

*Primary Examiner*—Jeffrey E. Russel
(74) *Attorney, Agent, or Firm*—Young & Thompson

(57) ABSTRACT

The invention pertains to novel peptide analogs suitable for inhibiting protein:prenyl transferases. As such they are therapeutically useful in e.g. inhibiting oncogenesis and other unwanted cell proliferation, and in supressing aberrant high signal transduction. The analogs comply with the following formula:

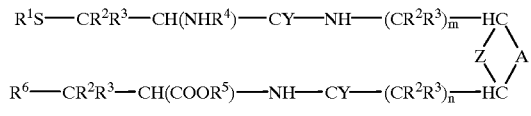

in which:
$R^1$ is hydrogen or a thiol-protecting group;
$R^2$ and $R^3$ are independently hydrogen or $C_1$–$C_4$ alkyl;
$R^4$ is hydrogen, $C_1$–$C_4$ alkyl, $C_1$–$C_4$ acyl or peptidyl;
$R^5$ is hydrogen or $C_1$–$C_4$ alkyl;
$R^6$ is hydrogen or optionally substituted $C_1$–$C_6$ alkyl;
A is a direct bond or an optionally substituted $C_1$–$C_4$ alkylene chain;
Y represents an oxo group or two hydrogen atoms;
Z is oxygen, sulphur, imino or $C_1$–$C_5$ alkyl-, aryl- or acylimino;
M is 0, 1 or 2;
N is 0 or 1.

7 Claims, 2 Drawing Sheets

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Cys Val Phe Met

PROTEIN:PRENYL TRANSFERASE INHIBITORS

BACKGROUND OF THE INVENTION

The present invention relates to analogs of tetrapeptides that inhibit protein:prenyl transferase. Protein:prenyl transferases are understood to comprise protein:farnesyl transferases, protein:geranylgeranyl transferases and any other enzymes capable of transferring prenyl groups to proteinaceous substrates.

DESCRIPTION OF THE RELATED ART

The post-translational modification of mammalian cell proteins involve thioether derivatisation of carboxyl-terminal cysteine residues by mevalonate-derived isoprenyl groups. Several of these prenylated proteins were identified as belonging to groups of related proteins: e.g. the nuclear lamins, low molecular weight GTP binding proteins, such as the ras-oncogene proteins and heteromeric G proteins (Schäfer et al., *Science* 245 (1989) 379–385). The prenyl group that was attached to a protein was identified as either farnesyl ($C_{15}$) or geranylgeranyl ($C_{20}$), probably depending on the recognition of the C-terminal amino acid sequence of the proteins involved, Lamins and p21$^{ras}$ proteins, 188 or 189 amino acid proteins which possess the consensus CAAX motif (C=cysteine, A=any amino acid having an aliphatic side chain and X=methionine, serine, glutamine or alanine) at the C terminus, are farnesylated, while several members of the rab proteins having C-terminal CC/CXC motifs, and of the heteromeric G-protein γ-subunits are geranylgeranylated.

The prenylation of these proteins seems to play a role in their association with membranes and nuclear envelopes, where they are processed further and/or perform their function. This was shown for example by blocking the mevalonate synthesis by HMG-CoA reductase inhibitors, which prevented proteolytic processing of the lamin A precursor (Beck et al., *J. Cell. Biol.* 110 (1990) 1489–1499) or resulted, in other studies, in the accumulation of non-prenylated p21$^{ras}$ precursor and the loss of transforming activity of oncogenic ras proteins. A review of the post-translational modification of proteins by isoprenoids in mammalian cells is given by Maltese W.A. in *FASEB J.* 4 3319–3329 (1990). The latter observation triggered the search for specific inhibitors of the farnesylation of p21$^{ras}$ in order to prevent its action in cells, where overexpression of this protein leads to tumour development, such as in colon carcinomas.

G proteins play a role in the receptor-mediated transduction of signals (such as growth modulation signals) over the plasma membrane, and other prenylated proteins, not yet identified, may have a function in cell cycle progression. There is some evidence as well that GTP binding proteins are involved in the regulation of intracellular protein traffic and secretion. There is even some suggestion that prenylated proteins play a role in the translational control of HMG-CoA reductase, the rate limiting enzyme of the isoprene and subsequent cholesterol synthesis.

The enzymes involved in the protein prenylation process, protein:prenyl transferases, are reported to use all-trans-farnesyl pyrophosphate (FPP) as a substrate for the addition of the farnesyl group to the protein. FPP is a substrate in the productoin of geranylgeranyl pyrophosphate, which is subsequently used in the synthesis of geranylgeranylated proteins. EP-A-540782 describes inhibitors for protein:farnesyl transferase based on prenyl pyrophosphate analogues.

A review of new therapeutic methods based on Ras farnesyltransferase and inhibitors thereof are described in Leonard in *J. Med. Chem.* 40 (1997), 2971–2990. A first group of potential inhibitors is based on the CAAX tetrapeptide motive of the ras proteins. The proposed analogues include CVFM (SEQ ID NO:1) as well as structures having reduced amide bonds and further deviations from pure tetrapeptide structures. Nigam et al (*J. Biol. Chem.* 268 (1993), 20695–98) reported that Cys-NH-CH$_2$-mC$_6$H$_4$-CO-Met inhibits Ras farnesyl transferase from human colon carcinoma with an IC$_{50}$ of 60 nM.

SUMMARY OF THE INVENTION

Novel tetrapeptide analogs have been found according to the invention, which are effective inhibitors of protein:prenyl transferases such as protein:farnesyl transferase and protein:geranylgeranyl transferases. The analogs are defined in the appending claims with reference to formula 1. These inhibitors are preferably not substrates for protein:prenyl transferases. The novel tetrapeptide s contain conformationally restricted dipeptide isoster moieties which have the potential to be unsusceptible towards enzymatic degradation.

DESCRIPTION OF THE PREFERRED EMBODIMENTS

Figure 1:
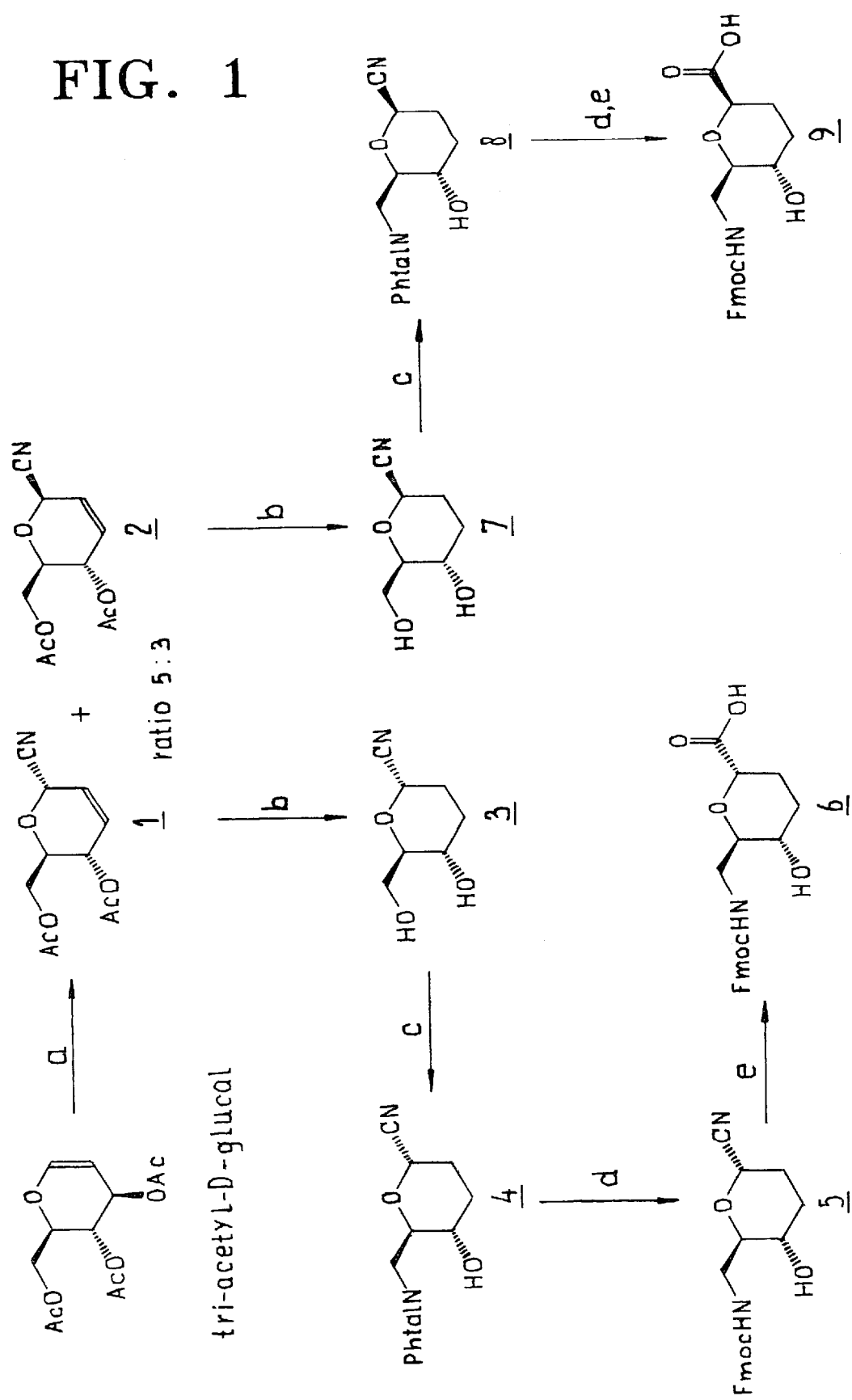
FIG. 1 shows scheme 1, the synthesis of the "trans" and "cis" sugar amino acids 6 and 9, respectively.
Figure 2:
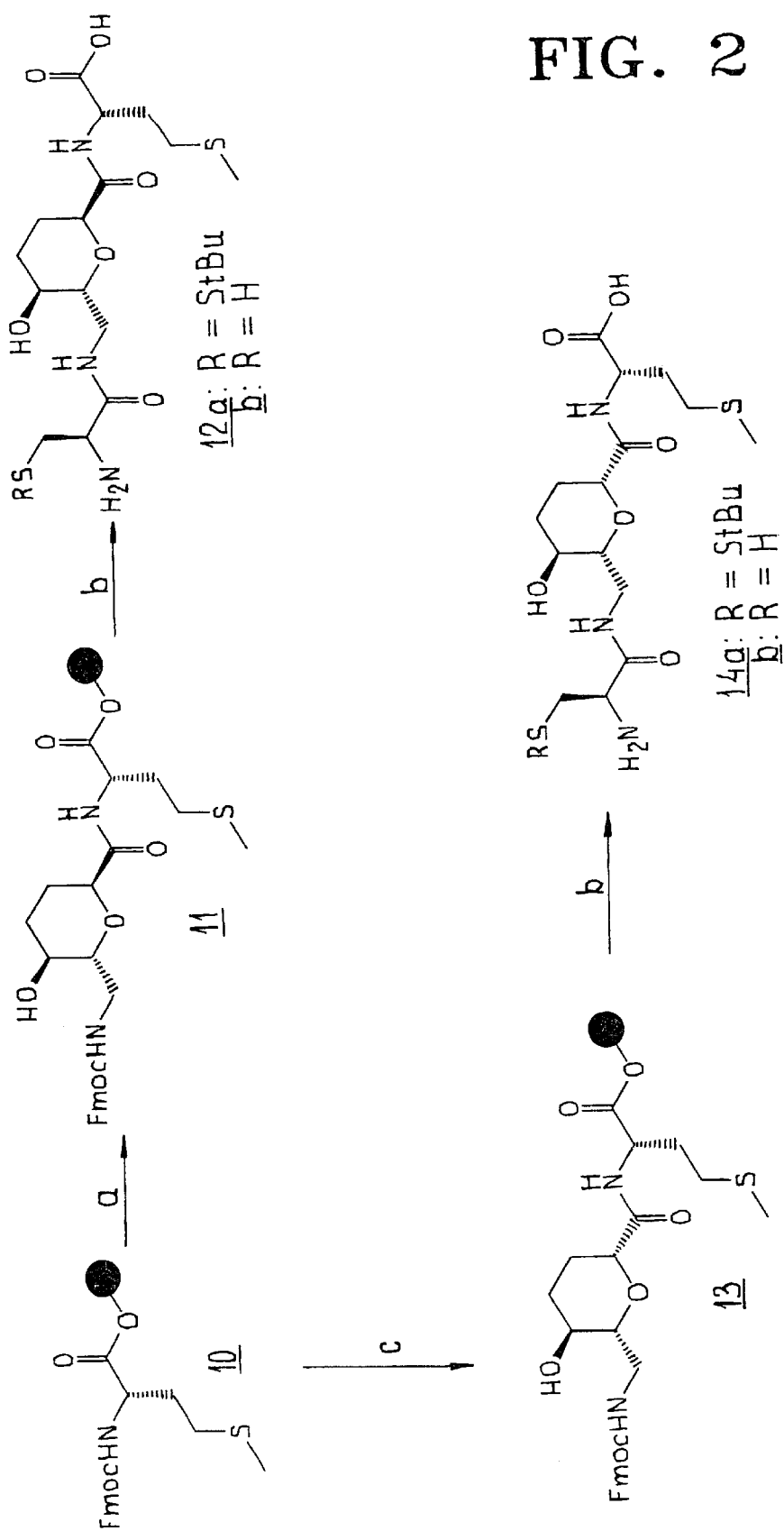
FIG. 2 shows scheme 2, the synthesis of the peptide analogs 12a, 12b, 14a, and 14b of the invention, as described in example 1.

An important feature of the peptide analogs of the invention is the presence of a heterocycle in the central part of the peptide analog. This heterocycle reduces the flexibility of the peptide analog, which was found to be important for being suitable as a protein:prenyl transferase inhibitor. Preferably, the heterocycle is at least saturated at the bridging atoms, so that cis-trans isomerism is present. More preferably, the heterocycle is fully saturated. Examples of suitable heterocycles include oxygen heterocycles such as furan, pyran and their dihydro and tetrahydro derivatives, 1,3- and 1,4-dioxane, oxirane, S-heterocycles such as thiolane, thiane, N-heterocycles such as pyrrolidine (optionally N-substituted), pyridine, piperidine, pyrazoline, azepine, diazepine, and mixed heterocycles such as morpholine, oxazolidine, thiazolidine and the like. The central ring unit is preferably a tetrahydropyran ring, preferably substituted with a hydroxy or alkoxy (e.g. methoxy, methylenedioxy, allyloxy, benzyloxy), amino, oxo, alkyl, or alkylidene group.

In the tetrapeptide analogues according to the invention, the N-terminal amino acid is cysteine or a cysteine derivative, such as cystine, S-alkylthio-cysteine or another disulphide compound such as an oxidised dimer. The C-terminal amino acid is preferably methionine, serine, homoserine, glutamine or alanine (especially for inhibition of protein:farnesyl transferase) or leucine or phenylalanine (especially for inhibition of protein:geranylgeranyl transferase). Preferred tetrapeptide analogues according to the invention are analogues that are expected to be specific for the inhibition of farnesylation or geranylgeranylation processes by the choice of the C-terminal amino acid.

The tetrapeptide analogs according to the invention can be prepared in a manner which is known per se. For example, they may be prepared by starting with the suitably protected central unit having the formula:

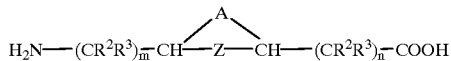

and coupling this unit to the terminal amino acids $R^1S\text{-}CR^2R^3\text{-}CH(NHR^4)\text{-}COOH$ and $R^6\text{-}CR^2R^3\text{-}CH(COOR^5)\text{-}NH_2$. Compounds in which CY is $CH_2$, rather than carbonyl, can be obtained by reduction or reductive amination, in a manner known per se. For example, these analogs may be prepared by starting with the suitably protected central unit having the formula:

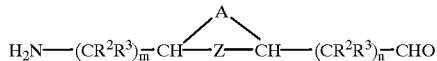

and reacting this unit under reductive conditions to the terminal amino acids:

and

It was found that the tetrapeptide analogs according to the invention are capable of inhibiting the farnesylation process. The heterocyclic (sugar-like) central building block of the analogs of the invention is structurally versatile, which means that various inhibitors can be easily generated through combinatorial chemistry. The bioavailability, stability against enzymatic degradation and inhibitory activity of these novel inhibitors will be better than for previously reported compounds.

The tetrapeptide analogs described above are useful as an active substance in a pharmaceutical composition intended to interfere with protein prenylation. As such, they are useful as inhibitors in processes such as oncogensis and other unwanted cell proliferation, e.g. in retinosis or atherosclerosis, and furthermore as suppressants of aberrant high signal transduction.

The pharmaceutical compositions containing the tetrapeptide analogs according to the invention may be formulated in a usual way, e.g. by associating the tetrapeptide analog with a suitable solid or liquid carrier and optional adjuvants or other active components. The composition may be suitable for oral administration (capsule, pill, tablet, gel, powder, sachet, syrup, solution, dispersion etc.) or may be injectable solution or another administration form. The composition may be administered to mammalians including man, in a dose which depends on the particular purpose of the administration and other conditions well known to the skilled person. A suitable dose in e.g. from 1 to 500 mg/kg body weight, especially from 10 to 200 mg/kg body weight. A dose can be administered in a single dosage or in several daily dosages.

Example 1

Synthesis of Protein-Farnesyl transferase Inhibitors

Tri-acetyl-D-glucal (Across) was treated with trimethylsilyl cyanide (TMSCN) under the influence of boron trifluoride ethyl etherate ($BF_3.OEt_2$) to obtain compounds 1 and 2, separated with silica gel column chromatography, in 50% and 30% yield, respectively (Scheme 1). Compound 1 was subsequently hydrogenated with 10% palladium on carbon (Pd/C) under a hydrogen atmosphere and deacetylated with sodium methanolate (NaOMe) to afford compound 3 in 78% overall yield. Compound 3 was transformed into compound 4, in 95% after silica gel column chromatography, under the action of phthalimide, triphenyl phosphine ($PPh_3$) and diethyl azodicarboxylate (DEAD). Compound 4 was treated with hydrazine followed by reaction with 9-fluorenylmethoxycarbonyl chloride (FmocCl) to produce compound 5 in 85% yield after silica gel column chromatography. Acid catalysed hydrolysis gave the "trans" sugar amino acid 6 in 80% yield. Proceeding in the same way, the "cis" sugar amino acid 9 was prepared from compound 2 (see Scheme 1). Fmoc-Met-wang resin 10 (0.06 mmol/g, Novabiochem) was treated with 20% piperidine in dimethylformamdie (DMF) and subsequently coupled with the "trans" compound 6 (5equiv.) under a standard solid phase peptide synthesis protocol (Atherton et al. *Solid Phase Synthesis: A Practical Approach*, IRL Press: Oxford, 1989) i.e. benzotriazole-1-yl-oxy-tris (dimethylamino) phosphonium hexafluorophosphate (BOP), 1-hydroxybenzotrizole (HOBt), diisopropylethylamine (DiPEA) in N-methylpyrrolidine (NMP) (Scheme 2). The obtained compound 11 was subsequently treated with 20% piperidine in DMF, coupled with FmosCys(S-tBu)-OH (Novabiochem) using the same reagents as mentioned above and cleaved form the solid support with trifluoroacetic acid (TFA)/ethanedithiol/-triisopropylsilane/phenol/H2O 96.4 0.8/1.2/0.8/0.8 v/v %. The obtained compound 12a was purified using preparative HPLC (Lichrosphere 100 RP18 end-capped (5μ), 10×250 mm, elution: linear gradient of 80% acetonitrile/water/0.1% TFA) and fully characterized with spectroscopic techniques. Compound 14a was obtained via the same protocol using "cis" sugar amino acid building block 9. The corresponding compounds 12b and 14b were obtained, in situ from reaction of dithiothreitol with 12a and 14a respectively, and the $IC_{50}$ values were determined as described in example 2.

Example 2

Assay of Protein:Farnesyl Transferase

PFT activity was determined using a C-terminal peptide of pre-p21$^{N\text{-}ras}$ coupled to sepharose beads as substrate (pep-Asep) as described previously (Cohen et al, *Biochem. Pharmacol.* 49 (1995), 839–845). The experimental conditions (25 μL reaction mixture) were as follows: 80 pmol/25 μL sepharose-coupled peptide, 0.7 μM of [3H]-FPP (American Radiolabeled Chemicals Inc; specific radioactivity 15 Ci/mmol) and 13 μL of rat brain enzyme preparation. Incubation was performed at 37° C. for 30 min. For the determination of $IC_{50}$ values of the FFP analogs, the assay was performed three times in the presence of different concentrations of the compounds 12a and 14a in duplicate.

We claim:

1. A peptide analog suitable as a protein:prenyltransferase inhibitor complying with formula 1:

$$R^1S-CR^2R^3-CH(NHR^4)-CY-NH-(CR^2R^3)_m-HC$$
$$\phantom{R^1S-CR^2R^3-CH(NHR^4)-CY-NH-(CR^2R^3)_m}Z\phantom{-}A$$
$$R^6-CR^2R^3-CH(COOR^5)-NH-CY-(CR^2R^3)_n-HC$$

$\quad$ 1 in which:
$R^1$ is hydrogen or a thiol-protecting group;
each $R^2$ and $R^3$ is independently hydrogen or $C_1$–$C_4$ alkyl;
$R^4$ is hydrogen, $C_1$–$C_4$ alkyl, $C_1$–$C_4$ alkyl or peptidyl;
$R^5$ is hydrogen or $C_1$–$C_4$ alkyl;
$R^6$ is hydrogen or $C_1$–$C_6$ alkyl optionally substituted with hydroxy, phenyl, hydroxyphenyl, indolyl, imidazolyl, mercapto, methylthio, amino, carboxyl, carbamoyl, ureido, amidino or guanidino;
A is a direct bond or a saturated $C_1$–$C_4$ alkylene chain, optionally interrupted by one or more oxygen, sulphur or nitrogen atoms, optionally substituted by hydroxy, oxo, $C_1$–$C_4$ alkyl, $C_1$–$C_4$ alkylidene, $C_1$–$C_4$ alkoxy, allyloxy, benzyloxy, $C_1$–$C_8$ acyloxy, $C_1$–$C_3$ alkyl(id)enedioxy, amino, $C_1$–$C_4$ alkylamino or $C_1$–$C_4$ hydroxyalkyl;
Y represents an oxo group or two hydrogen atoms;
Z is oxygen, sulphur, imino or $C_1$–$C_8$ alkyl-, aryl-or acylimino;
m is 0, 1 or 2;
n is 0 or 1.

2. The peptide analog according to claim 1, in which one or more of the following definitions apply:
at least one of $R^2$ and $R^3$ is hydrogen;
$R^4$ is hydrogen;
$R^5$ is hydrogen;
$R^6$ is methylthiomethyl, isopropyl, hydroxymethyl or phenyl;
A is saturated trimethylene chain, optionally substituted by one or more hydroxy groups;
Y is oxo;
Z is oxygen;
m is 1; and
n is 0.

3. The peptide analog according to claim 1, in which the two substitutents:

$$R^1S-CR^2R^3-CH(NHR^4)-CY-NY-(CR^2R^3)m-\qquad 2$$

and $$R^6-CR^2R^3-CH(COOR^5)-NH-CY-(CR^2R^3)n-$$

are bound in the cis position to the ring system having formula 4:

$$\begin{array}{c}-HC\\ \phantom{-}Z\phantom{-}A.\\ -HC\end{array}$$

4. The peptide analog according to claim 1, in which said thiol-protecting group $R^1$ is selected from the group consisting of $C_1$–$C_8$ alkylthio and aralkylthio groups and a group having formula 1 minus $R^1$.

5. A method of treatment comprising inhibiting protein:prenyltransferase, comprising administering to a subject in need of such treatment an effective dose of a peptide analog according to claim 1.

6. A pharmaceutical composition containing a peptide analog according to claim 1, together with a pharmaceutically acceptable carrier.

7. A method of assaying protein:prenyltransferase activity in a biological sample, comprising the step of contacting the sample with a peptide analog according to claim 1.

* * * * *